United States Patent
Delie et al.

(10) Patent No.: US 9,664,631 B2
(45) Date of Patent: May 30, 2017

(54) MOISTURE SENSOR FOR A FORAGE HARVESTER

(71) Applicant: CNH Industrial America LLC, New Holland, PA (US)

(72) Inventors: Dries Delie, Poelkapelle (BE); Didier O. M. Verhaeghe, Ypres (BE); Benoit Debilde, Bruges (BE); Bert J. F. Paquet, Bruges (BE)

(73) Assignee: CNH Industrial America LLC, New Holland, PA (US)

( * ) Notice: Subject to any disclaimer, the term of this patent is extended or adjusted under 35 U.S.C. 154(b) by 69 days.

(21) Appl. No.: 14/623,346

(22) Filed: Feb. 16, 2015

(65) Prior Publication Data

US 2015/0233855 A1    Aug. 20, 2015

(30) Foreign Application Priority Data

Feb. 17, 2014  (BE) .................................. 2014/0105

(51) Int. Cl.
| | |
|---|---|
| *G01N 27/04* | (2006.01) |
| *G01N 33/00* | (2006.01) |
| *G01N 33/02* | (2006.01) |
| *A01D 41/127* | (2006.01) |
| *A01D 43/08* | (2006.01) |

(52) U.S. Cl.
CPC ....... *G01N 27/048* (2013.01); *G01N 33/0098* (2013.01); *G01N 33/025* (2013.01); *A01D 41/127* (2013.01); *A01D 43/085* (2013.01)

(58) Field of Classification Search
CPC ... G01N 27/048; A01D 41/127; A01D 43/085
USPC .......................................................... 324/694
See application file for complete search history.

(56) References Cited

U.S. PATENT DOCUMENTS

| | | | |
|---|---|---|---|
| 3,761,810 A | * | 9/1973 | Fathauer |
| 6,389,884 B1 | | 5/2002 | Diekhan et al. |
| 6,437,582 B1 | | 8/2002 | Rode et al. |

(Continued)

FOREIGN PATENT DOCUMENTS

| | | |
|---|---|---|
| BR | PI0801428 A2 | 11/2009 |
| DE | 3306460 A1 | 8/1984 |

(Continued)

*Primary Examiner* — Walter L Lindsay, Jr.
*Assistant Examiner* — Milton Gonzalez
(74) *Attorney, Agent, or Firm* — Peter K. Zacharias; Patrick M. Sheldrake (57) ABSTRACT

A moisture sensor for a forage harvester is described, the moisture sensor comprising a sensing device, a processing unit and an output terminal. The sensing device is configured to sense an electrical characteristic of a harvested crop and generate a sensor signal representative of the electrical characteristic. The processing unit is configured to receive the sensor signal from the sensing device and to process the sensor signal to derive a moisture level of the harvested crop. The output terminal is connected to the processing unit for outputting an output signal representative of the moisture level as derived by the processing unit. Each operating mode for the sensing device having a different moisture level sensitivity characteristic, and receiving an operating parameter and selecting an operating mode of the plurality of operating modes for the sensing device, based on the operating parameter.

11 Claims, 4 Drawing Sheets

(56) References Cited

U.S. PATENT DOCUMENTS

| | | | |
|---|---|---|---|
| 6,487,836 | B1 | 12/2002 | Coers et al. |
| 6,686,749 | B2 | 2/2004 | Rains et al. |
| 7,231,814 | B2 | 6/2007 | Platon et al. |
| 7,340,996 | B1 | 3/2008 | Viaud |
| 8,610,445 | B2 | 12/2013 | Diekhans et al. |
| 2009/0120202 | A1* | 5/2009 | Diekhans ............. A01D 43/085 |

FOREIGN PATENT DOCUMENTS

| | | |
|---|---|---|
| DE | 10204941 A1 | 8/2003 |
| JP | S5870151 A1 | 4/1983 |
| JP | 2001078537 A | 3/2001 |
| JP | 2003189733 A | 7/2003 |
| JP | 2006254758 A | 9/2006 |

* cited by examiner

MOISTURE SENSOR FOR A FORAGE HARVESTER

CROSS REFERENCE TO RELATED APPLICATIONS

This patent application claims priority under 35 U.S.C. §119 to BE 2014/0105 filed on Feb. 17, 2014 titled, "Moisture Sensor for a Forage Harvester" and having Dries Delie, Didier Verhaeghe, Benoit Debilde, and Bert J. F. Paquiet as the inventors. The full disclosure of BE 2014/0105 is hereby fully incorporated herein by reference.

FIELD OF THE INVENTION

The invention relates to the field of moisture sensors and more specifically to the application of such sensors in agricultural harvesters such as combine or forage harvesters.

BACKGROUND OF THE INVENTION

The present invention relates to the use of moisture sensors in agricultural equipment such as combine or forage harvesters. Such equipment is often equipped with a moisture sensor, e.g. mounted in a spout of the harvester, to determine a moisture level of the harvested crop. Typically, such moisture sensors determine an electrical characteristic such as a resistance or capacitance measured between two fixed electrodes. As an example, reference can e.g. be made to EP2057883 disclosing a resistance (or conductance) based measurement of a moisture level of a harvested crop. The use of such a sensor arrangement has however been found to give poor results with respect to the achievable accuracy. Typically, such sensors only provide satisfactory results in a limited moisture level range. In addition, the sensed property, e.g. a resistance or capacitance value may need to be calibrated or corrected to obtain a sufficiently accurate determination of the moisture level. Such correction may e.g. require that additional measurements such as temperature measurements need to be made.

SUMMARY OF THE INVENTION

It would be desirable to provide a moisture sensor suitable for use in an agricultural equipment such as a combine or forage harvester which at least partly mitigates the problems as mentioned and thus enables a more accurate determination of a moisture level of a harvested crop.

To address this, in a first aspect of the invention, a moisture sensor for harvested crop is provided, the moisture sensor comprising:
  a sensing device configured to sense an electrical characteristic of the harvested crop, and generate a sensor signal representative of the electrical characteristic;
  a processing unit configured to receive the sensor signal from the sensing device, the processing unit further being configured to process the sensor signal to derive a moisture level of the harvested crop;
  an output terminal connected to the processing unit for outputting an output signal representative of the moisture level as derived by the processing unit,
  wherein the sensing device is further configured to operate in one of a plurality of different operating modes when sensing the electrical characteristic, each operating mode having a different moisture level sensitivity characteristic, and wherein the processing unit is further configured to receive an operating parameter associated with the harvested crop and to select an operating mode of the plurality of different operating modes for the sensing device, based on the operating parameter.

In accordance with the present invention, a moisture sensor is provided which can operate in different operating modes, whereby the operating mode is selected based on an operating parameter associated with the harvested crop. As such, depending on the operating conditions of the harvester onto which the sensor is applied, the operating conditions being represented by an operating parameter, an appropriate operating mode can be selected and a sensing of an electrical characteristic of the harvested crop can be performed in the best suited operating mode.

The sensor comprises a sensing device which can determine an electrical characteristic of the harvested crop.

As an example, the sensor can comprise a set of electrodes arranged to determine a resistance or capacitance value, in general an impedance value, of the crop.

In an embodiment, the sensor comprises an array of electrodes configured such that different pairs of electrodes can be selected for measuring the electrical characteristic of the crop. By selecting a different pair of electrodes, the sensor of such embodiment is understood as operating in a different operating mode. The different pairs of electrodes may be spaced at different distances apart.

In an embodiment, the different operating modes correspond to the application of different frequencies or different frequency ranges when sensing the electrical characteristic. In such embodiment, the sensing device can e.g. comprise a current or voltage source which can operate at different frequencies or different frequency ranges. In such embodiment, the different operating modes may e.g. include a first operating mode whereby a DC voltage or current is applied to sense the electrical characteristic and a second operating mode whereby an AC voltage or current is applied to sense the electrical characteristic.

In an embodiment, the electrical characteristic measured is a resistance value measured between two electrodes that are spaced apart over a fixed distance. In order to determine the resistance value of the harvested crop, the harvested crop during use bridging the distance between the electrodes, use may be made of a Wheatstone bridge. In such arrangement, the sensor may operate in different operating modes by applying different reference resistances in the Wheatstone bridge. By selecting a different reference resistance, the sensitivity (and thus accuracy) of the measurement can be altered, e.g. depending on an operating parameter associated with the harvested crop.

In accordance with the present invention, various parameters may be suited as operating parameters and thus applied to select the appropriate operating mode. Such operating parameters e.g. including the type or crop that is harvested or an initially determined moisture level of the harvested crop. The operating parameter may also comprise a GPS signal indicating a location of the harvested crop. In such embodiment, the processing unit of the moisture sensor may be configured to derive, based on the GPS signal, the type or crop that is harvested, e.g. by accessing a database containing such information.

It has been observed by the inventors that known moisture sensors as applied in agricultural equipment are typically only suited to be applied to determine a moisture level of a harvested crop in a limited operating range. Moisture sensors may e.g. be configured to provide satisfactory results when determining a moisture level ranging from 0 to 25% while being unsuited to accurately determining a moisture level when the moisture level is in the range of >75%.

Therefore, in accordance with the present invention, the moisture sensor comprises a sensing device which can be operated in different operating modes, the operating modes having a different moisture level sensitivity characteristic.

In accordance with the present invention, the moisture sensor comprises a processing unit configured to receive a sensor signal from the sensing device, the processing unit further being configured to process the sensor signal to derive a moisture level of the harvested crop. The sensor signal as provided by the sensing device represents an electrical characteristic of the harvested crop, e.g. a resistance or conductance value, or a measured capacitance value. In accordance with the present invention, the processing unit is further configured to select an operating mode for the sensing device, based on the operating parameter as provided to the processing unit.

In an embodiment, the type of crop is applied as the operating parameter. In general, a typical moisture level range can be associated with certain types of crop. As such, when the type or harvested crop is known (e.g. corn or grain or grass), one can expect that the moisture level is substantially within a specific range. The appropriate operating mode, having a sufficient moisture level sensitivity in that specific range may thus be selected, based on the operating parameter, i.e. the type of crop in this embodiment.

In another embodiment, the moisture level itself is applied as the operating parameter. In such embodiment, the sensing device may be operating in a particular operating mode and providing a sensor signal to the processing unit. Based on the moisture level as determined by the processing unit based on the sensor signal, the processing unit may select a more suited operating mode for the sensing device. Subsequently, the sensing device may operating in the more suited operating mode and provide a further sensor signal to the processing unit to assess the moisture level. As such, an iterative process may be conducted to ensure the application of the best suited operating mode.

In an embodiment, a substantially continuous assessment is made by the processing unit of whether the operating mode of the sensing device is the most suited.

In an embodiment of the present invention, the sensing device provides in different electrode configurations (corresponding to different operating modes) for sensing the electrical characteristic of the harvested crop in the different operating modes. As an example, the sensing device may comprise an array of electrodes, whereby different pairs of electrodes, having different distances between the electrodes forming a pair, can be selected, based upon the operating parameter.

In an embodiment, the sensing device as applied in the moisture sensor according to the present invention, may be configured to sense the electrical characteristic using different supply sources such as current or voltage sources; by applying a variable frequency voltage or current source, the electrical characteristic can e.g. be sensed at different frequency, corresponding to a sensing in different operating modes. In this respect it is worth noting that a moisture level sensitivity may depend on the applied frequency when sensing an electrical characteristic using a variable frequency voltage or current source.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

Figure 1:
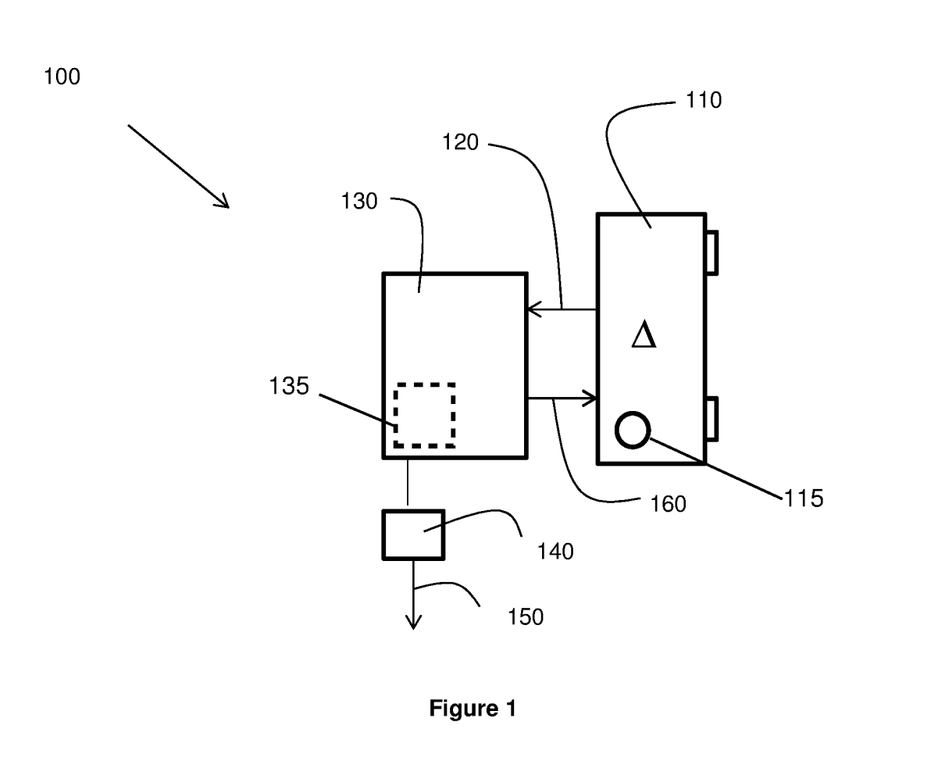
FIG. 1 depicts an embodiment of a moisture sensor according to the present invention.

FIG. 1 depicts an embodiment of a moisture sensor 100 according to an embodiment of the present invention. The moisture sensor 100 as schematically shown comprises a sensing device 110 configured to sense an electrical characteristic of a harvested crop, and generate a sensor signal 120 representative of the electrical characteristic. In an embodiment, the sensing device 110 may e.g. comprise one or more pairs of electrodes 115 for sensing the electrical characteristic, e.g. a resistance or capacitance value of the harvested crop. The moisture sensor further comprises a processing unit 130 configured to receive the electrical signal 120 from the sensing device 110, the processing unit 130 further being configured to process the sensor signal 120 to derive a moisture level of the harvested crop. In order to provide the sensor signal 120 from the sensing device 110 to the processing unit 130, a wired or wireless connection can be provided between the sensing device 110 and the processing unit 130.

The moisture sensor 100 as shown further comprises an output terminal 140 connected to the processing unit 130 for outputting an output signal 150 representative of the moisture level as derived by the processing unit 130. Such an output signal may e.g. be provided to a display (not shown) or may be logged. In accordance with the present invention, the sensing device 110 is further configured to operate in one of a plurality of different operating modes (schematically indicated by the symbol A) when sensing the electrical characteristic, each operating mode having a different moisture level sensitivity characteristic. In accordance with the present invention the processing unit 130 is further configured to receive an operating parameter and to select an operating mode of the plurality of operating modes for the sensing device 110, based on the operating parameter. In an embodiment, this may be realized by providing a control signal 160 from the processing unit 130 to the sensing device 110. The control signal may, in such embodiment, control the operating mode of the sensing device. In an other embodiment, the electrical signal 120 of the sensing device 110 may comprise multiple signals corresponding to multiple measurements taken in different operating modes. In such embodiment, the processing unit may select, based on the operating parameter, the most appropriate signal (corresponding to a measurement at the most appropriate operating mode) to derive the moisture level.

It has been devised by the inventors that, in general, a moisture sensor having a single measurement or operating mode may be insufficient to determine, in a sufficiently accurate manner, the moisture level of a harvested crop.

The moisture sensor according to the present invention is configured to operate in different operating modes, whereby the operating mode is selected, based on an operating parameter which is received by the processing unit 130, to ensure that the sensing device 110 is operating in a appropriate mode, having a sufficiently high sensitivity with respect to the moisture level.

In accordance with the present invention, moisture level sensitivity characteristic is used to denote the capability to distinguish between different moisture levels, based on a sensed electrical characteristic of the harvested crop.

Figure 2:
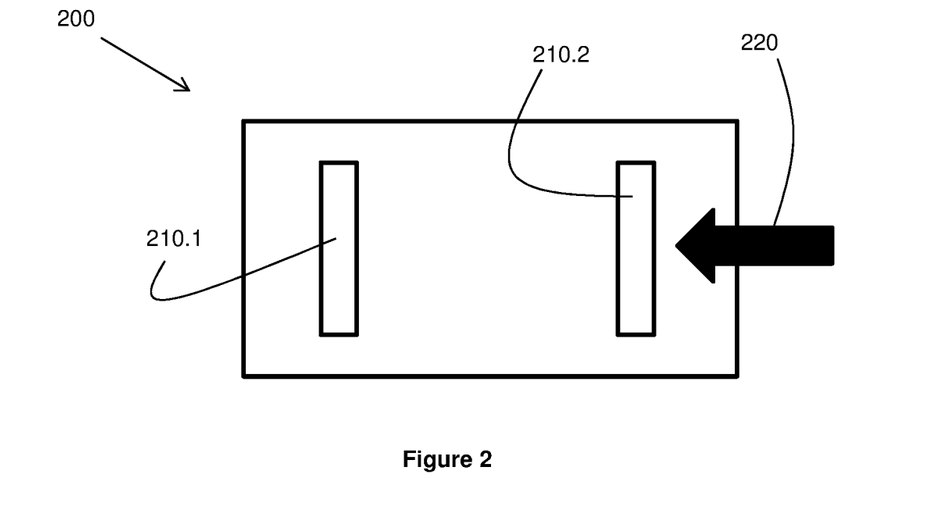
FIG. 2 depicts a top view of a moisture sensor according to the present invention.

To illustrate this, a sensing device having two electrodes is considered, the electrodes being separated from each other over a fixed distance. FIG. 2 schematically shows a front view of such a sensing device 200, including two plate shaped electrodes 210.1 and 210.2. Arrow 220 schematically indicates a direction of the flow of harvested crop, when the sensor is e.g. applied in a spout of a harvester such as a forage harvester. As an electrical characteristic, the impedance as observed between both electrodes can be measured.

Figure 3:
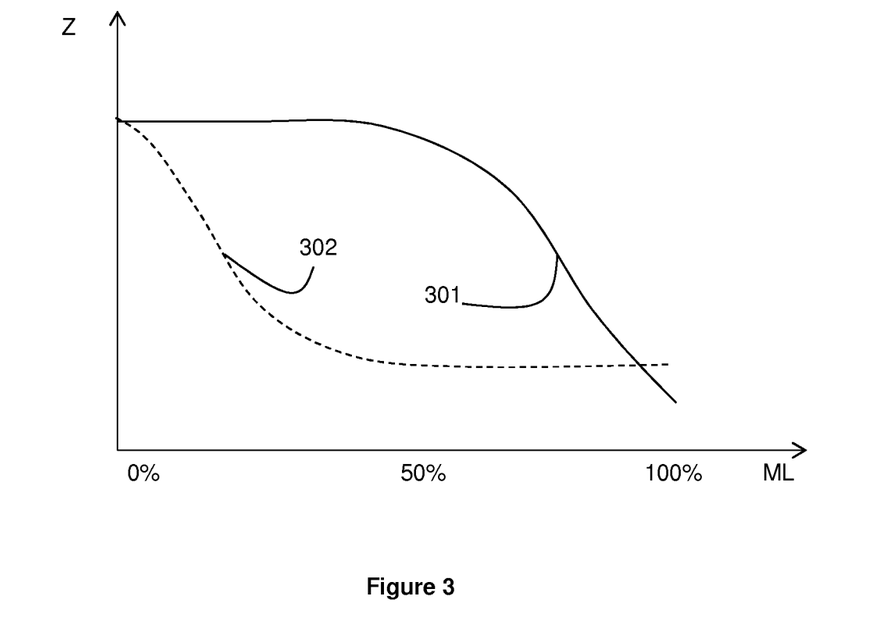
FIG. 3 depicts two impedance vs. moisture level characteristics as obtained when operating in two different operating modes.

In FIG. 3, two graphs are schematically shown, representing the measured electrical characteristic (i.e. the impedance Z), for two different operating modes, as a function of the moisture level (ML). Graph 301 in FIG. 3 schematically represent the impedance (Z) as measured between the electrodes 210.1 and 210.2 of the sensing device when operating in DC-mode, i.e. a DC impedance (resistance) measurement is performed, whereas graph 302 represents the impedance (Z) as measured when operating in an AC-mode. As can be derived, when considering the graphs, the AC operating mode provides in a comparatively high sensitivity when the moisture level is low, whereas the DC operating mode provides is a comparatively high sensitivity when the moisture level is high. As can be seen from graph 1, the measured impedance (resistance) hardly changes when the moisture level is below 40%, thus resulting in a poor sensitivity to determine the moisture level in that range. Similarly, when performing an AC measurement as represented by graph 2, the measured impedance hardly changes when the moisture level is above 60%, thus resulting in a poor sensitivity to determine the moisture level in that range.

Given such measurement characteristics over a desired moisture level range, one can determine, for each operating mode, a characteristic representing the sensitivity to determine a particular moisture level, referred to in the present invention as the moisture level sensitivity characteristic. Such characteristic thus describing the suitability to apply a particular operating mode in a particular moisture level range. Given the measurement characteristics of the different operating modes, a moisture level sensitivity characteristic may be derived and represented in various ways.

As an example, the moisture level sensitivity characteristic can be determined as the slope or derivative of the measurement characteristic as e.g. shown in FIG. 3. The slope or derivative at a particular moisture level may then be considered to represent the sensitivity to measure that moisture level. A slope or derivative value near zero would thus imply a poor sensitivity to determine the particular moisture level.

In an embodiment of the sensor according to the present invention, the processing unit 130 is provided with a memory unit 135 comprising the moisture level sensitivity characteristics of the different operating modes. These characteristics may be implemented in various ways in the processing unit 130. As an example, the characteristics may be implemented by indicating, for each operating mode, the moisture level range in which the operating mode may be used.

Referring to the graphs of FIG. 3, a possible implementation of the moisture level sensitivity characteristic in a processing unit of a moisture sensor according to the invention could be to indicate that the AC operating mode is to be used when the moisture level is expected to be below 50% and to indicate that the DC operating mode is to be used when the moisture level is expected to be above 50%.

In an embodiment, the processing unit of the moisture sensor according to the present invention configured to determine an estimated moisture level or moisture level range, based on the operating parameter and to select the operating mode, based on the estimated moisture level or moisture level range.

As an example, the operating parameter as provided to the processing unit may be the type of crop that is harvested. When grass is harvested, the moisture level may typically be in the range of 5-15%, whereas, when corn is harvested, the moisture level may typically be in the range of 75-85%.

In such embodiment, the processing unit may thus be configured to determine, when the type of crop is inputted as an operating parameter (e.g. inputted by the operator of the harvester via a user interface connected to the processing unit), an estimated (or expected) moisture level or moisture level range and subsequently determine the appropriate operating mode. This may e.g. be implemented as a table in a memory unit of the processing unit.

As another example, the sensor signal as provided by the sensing device may be applied as the operating parameter. In such an arrangement, the moisture sensor according to the present invention may initially start operating in a default operating mode (e.g. a DC operating mode as described by graph 301 of FIG. 3) and provide a sensor signal to the processing unit. The processing unit may then determine, based on the sensor signal, determine the moisture level, given the measurement characteristic associated with the operating mode. Given the determined moisture level, the processing unit may then determine whether the initial operating mode is the mode best suited to determine the moisture level.

Assuming e.g. that the initial operating mode is a DC operating mode as represented by graph 301 in FIG. 3 and that the determined moisture level would be 15%. Given the moisture level sensitivity characteristic of the DC operating mode, it is clear that another operating mode e.g. an AC operating mode as represented by graph 302 in FIG. 3, could be more suited to accurately determine the moisture level.

In order to operate in different operating modes, the sensing device 110 of the moisture sensor 100 according to the present invention may be equipped with a variable frequency supply source 115, such as a voltage or current source 115. Depending on the most suited operating mode, as determined by the processing unit 130 of the moisture sensor 100, an appropriate supply signal may be applied to a pair of electrodes of the sensing device 110, to sense the electrical characteristic with the appropriate frequency.

As an alternative to applying a variable frequency supply source, a differentiation in the possible operating modes may also be obtained by applying a sensing device that is provided with an array of electrodes, whereby different pairs of electrodes can be selected to determine the electrical characteristic of the harvested crop.

Figure 4:
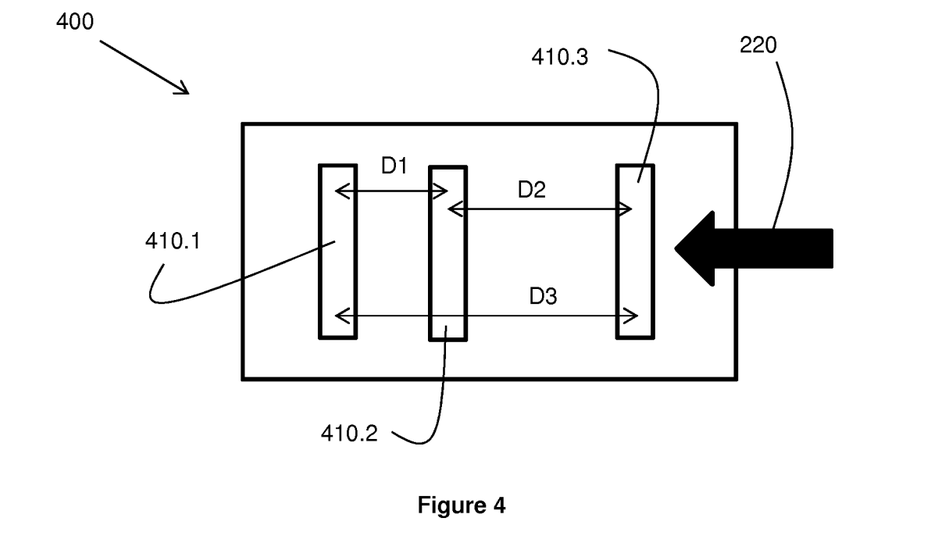
FIG. 4 depicts a top view of another moisture sensor according to the present invention.

FIG. 4 schematically shows a top view of an embodiment of a sensing device 400 having an array of electrodes 410.1-401.3. Arrow 420 schematically indicates a flow of the harvested crop, during use of the sensor. In the embodiment as shown, the sensing device 400 is configured to measure an electrical characteristic of the harvested crop by applying an pair of electrodes of the array. For the array as shown, three different pairs of electrodes may thus be applied, corresponding to operating in three different operating modes, having a different moisture level sensitivity characteristic. As can be seen from FIG. 4, each pair of electrodes selected from the array of electrodes 410.1-401.3 will have a different distance between the respective electrodes, i.e. D1≠D2≠D3. For a given moisture level of the harvested crop, the selection of the different pairs of electrodes will result in a different measured resistance or impedance and a different sensitivity. When electrode-pair 410.1-410.3 is selected, the distance between the electrodes is comparatively high. Such configuration may e.g. be the most suited to determine the moisture level of crops having a comparatively high moisture level. When an expected moisture level is low, it may be beneficial to select an electrode-pair having the electrodes closer together, such as in electrode-pair 410.1-410.2.

Figure 5:
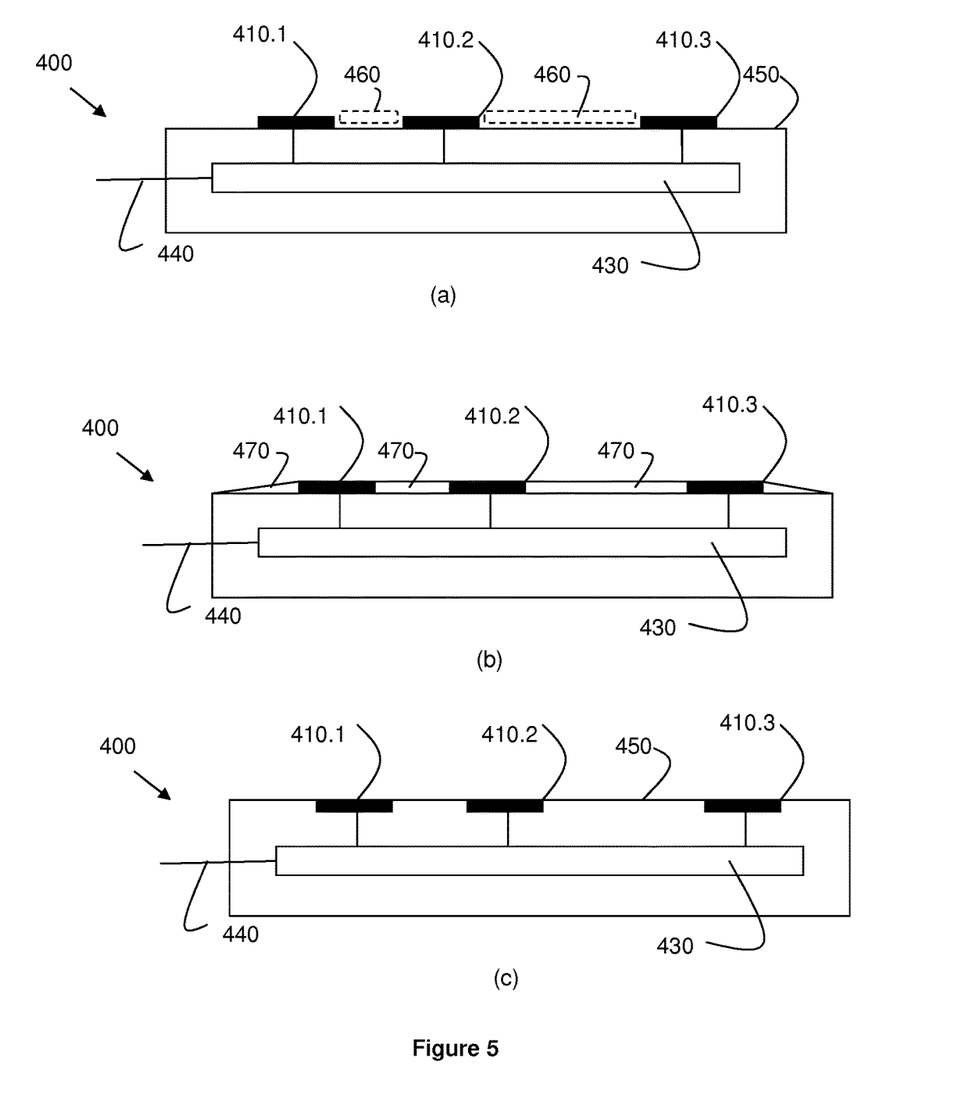
FIGS. 5(a), 5(b), and 5(c) depict cross-sectional side views of embodiments of the moisture sensor of FIG. 4.

In FIG. 5, several possible cross-sectional side views (a), (b), and (c) of the sensing device 400 of FIG. 4 are schematically shown.

In FIG. 5, the electrodes 410.1-410.3 are shown and connected to a switching arrangement 430 configured to select, by appropriate switching (e.g. by using electronic switches, not shown), the required configuration of electrodes and enabling to provide a sensor signal 440 to a processing unit of the moisture sensor.

In the embodiment as shown in FIG. 5(a), the electrodes are mounted to a top surface 450 of the sensing device 400. In this embodiment, as can be seen, the electrodes are provided with rather sharp corners. This may result in harvested crop sticking near the corners of the electrodes or the areas 460 between the electrodes. Such sticking of the crop may adversely affect the accuracy of the moisture level as determined. In order to avoid or mitigate this sticking, the corners of the electrodes may be rounded and/or, as shown in FIGS. 5(b) and 5(c):

the areas between the electrodes and adjacent the electrodes (470) is filled with a non-conducting material 470 or the electrodes may be embedded in the top surface 450 of the sensing device 400.

By doing so, a substantially even or smooth top surface is obtained, to which harvested crop may not stick easily.

Figure 6:
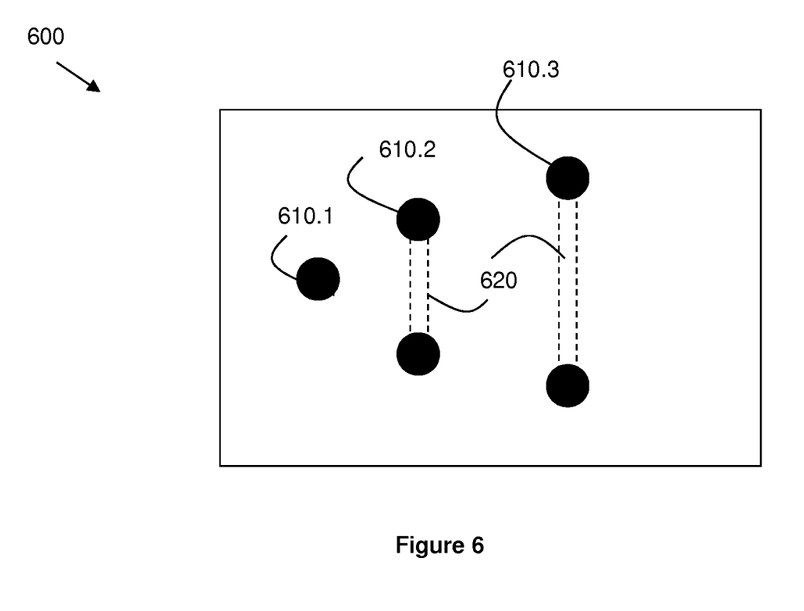
FIG. 6 depicts yet another top view of a moisture sensor according to the present invention.

FIG. 6 schematically shows a top view of another sensing device 600 as can be applied in a moisture sensor according to the invention. The sensing device comprises three electrodes 610.1-610.3, whereby electrodes 610.2 and 610.3 have two areas (indicated by the black circles) that are, during use, in contact with the harvested crop, the two areas being connected to each other below the top surface of the sensing device 600, indicated by the connection 620.

In the embodiment as shown, the processing unit of the moisture sensor can either select an operating mode whereby an impedance is measure between electrode 610.1 and electrode 610.2 or an operating mode whereby an impedance is measure between electrode 610.1 and electrode 610.3, e.g. depending on the type of crop that is harvested.

In an embodiment, the processing unit of the moisture sensor is further configured to receive a temperature signal representative of the temperature of the harvested crop and to determine the moisture level of the harvested crop, based on the temperature signal. When mounted to an agricultural harvester, the processing unit may e.g., via an input terminal, receive a temperature signal of a temperature sensor mounted to the harvester, the temperature sensor sensing the outdoor temperature.

As an alternative, the moisture sensor may be equipped with a temperature sensor, e.g. incorporated in the sensing device of the moisture sensor, the temperature sensor being configured to, during use, determine the temperature of the harvested crop that passes the sensing device.

As mentioned, the operating parameter may be the type of crop that is harvested. As an alternative, the operating parameter may comprise a GPS signal representing a location of the harvester. In such arrangement, the processing unit of the moisture sensor may being configured to derive, using the GPS signal, the type of crop that is harvested, e.g. by accessing a database containing the location and type of crops to be harvested.

The moisture sensor according to the invention enables a more accurate determination of the moisture level of a harvested crop, because the moisture sensor according to the present invention can be operated in different operating modes, whereby the operating mode is selectable, based on an operating parameter associated with the harvested crop.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

A single processor or other unit may fulfill the functions of several items recited in the claims.

The invention claimed is:

1. A moisture sensor for a harvested crop, the moisture sensor comprising:
   a sensing device that senses an electrical characteristic of the harvested crop, and generates a sensor signal representative of the electrical characteristic;
   a processing unit that receives the sensor signal from the sensing device, the processing unit processes the sensor signal to derive a moisture level of the harvested crop; and
   an output terminal connected to the processing unit for outputting an output signal representative of the moisture level as derived by the processing unit,
   wherein the sensing device is operable in one of a plurality of different operating modes when sensing the electrical characteristic, each operating mode having a different moisture level sensitivity characteristic, and wherein the processing unit receives an operating parameter associated with the harvested crop and based on the operating parameter, selects an operating mode from the plurality of different operating modes for the sensing device, wherein the sensing device comprises a variable frequency current or voltage source for sensing the electrical characteristic, the different operating modes corresponding to the use of different frequencies or frequency ranges of the variable frequency current or voltage source, and wherein the plurality of different operating modes includes at least a first operating mode whereby a DC voltage or current is applied to sense the electrical characteristic and a second operating mode whereby an AC voltage or current is applied to sense the electrical characteristic.

2. The moisture sensor according to claim 1, wherein the sensing device comprises an array of electrodes for sensing the electrical characteristic and wherein the processing unit is configured to select a pair of electrodes of the array of electrodes for sensing the electrical characteristic.

3. The moisture sensor according to claim 1, wherein the sensor comprises an input terminal, connected to the processing unit, for receiving an input signal representing the operating parameter.

4. The moisture sensor according to claim 1, wherein the plurality of different operating modes correspond to the use of different configurations of the sensing device.

5. The moisture sensor according to claim 1, wherein an outer surface of the sensing device which is, during use, in contact with the harvested crop, is substantially smooth.

6. The moisture sensor according to claim 1, wherein the processing unit comprises a memory unit that processes the moisture level sensitivity characteristics of the different operating modes, the processing unit being configured to select the operating mode of the plurality of different operating modes for the sensing device, based on the operating parameter and the different moisture level sensitivity characteristics, and wherein the processing unit further:

determines an estimated moisture level or moisture level range, based on the operating parameter and;

selects the operating mode, based on the estimated moisture level or moisture level range.

7. The moisture sensor according to claim 1, wherein the operating parameter comprises the sensor signal.

8. The moisture sensor according to claim 7, wherein the sensing device is configured to start up in a default operating mode to generate the sensor signal, the processing unit being configured to determine an initial moisture level from the sensor signal and select an operating mode for the sensing device, based on the sensor signal.

9. The moisture sensor according to claim 7, wherein the processing unit is further configured to receive a temperature signal representative of the temperature of the harvested crop and to determine the moisture level of the harvested crop, based on the temperature signal.

10. The moisture sensor according to claim 7, wherein the operating parameter comprises a type of crop that is harvested.

11. The moisture sensor according to claim 1, wherein the operating parameter comprises a GPS signal representing a location of the harvested crop, the processing unit being configured to derive, using the GPS signal, a type of crop that is harvested.

* * * * *